United States Patent
Bruecher

(10) Patent No.: US 9,068,157 B2
(45) Date of Patent: Jun. 30, 2015

(54) SAMPLING DEVICE

(75) Inventor: Daniel Bruecher, Duesseldorf (DE)

(73) Assignee: Infors AG, Bottmingen (CH)

( * ) Notice: Subject to any disclaimer, the term of this patent is extended or adjusted under 35 U.S.C. 154(b) by 326 days.

(21) Appl. No.: 12/894,915

(22) Filed: Sep. 30, 2010

(65) Prior Publication Data

US 2011/0079095 A1  Apr. 7, 2011

(30) Foreign Application Priority Data

Oct. 1, 2009 (DE) .......................... 10 2009 043 699

(51) Int. Cl.
*C12M 1/26* (2006.01)

(52) U.S. Cl.
CPC ................... *C12M 33/04* (2013.01)

(58) Field of Classification Search
CPC . G01N 1/12; G01N 1/2035; G01N 2001/002; G01N 2001/005
USPC ...................................................... 73/864.63
See application file for complete search history.

(56) References Cited

U.S. PATENT DOCUMENTS

| 5,624,638 | A | 4/1997 | Negrotti |
| 5,948,998 | A | 9/1999 | Witte et al. |
| 8,033,187 | B2 | 10/2011 | Sann et al. |
| 2002/0129858 | A1 | 9/2002 | Meyer et al. |
| 2005/0084410 | A1 | 4/2005 | Meyer et al. |
| 2005/0214927 | A1 | 9/2005 | Haley |
| 2007/0088216 | A1* | 4/2007 | Pfeiffer et al. ................. 600/468 |
| 2007/0193376 | A1 | 8/2007 | Sharma et al. |

FOREIGN PATENT DOCUMENTS

| DE | 26 50 405 A1 | 5/1978 |
| DE | 42 05 826 A1 | 9/1993 |
| DE | 10 2004 001 916 A1 | 8/2005 |
| DE | 10 2004 045 916 A1 | 3/2006 |
| DE | 10 2004 045 785 B3 | 5/2006 |
| DE | 10 2005 020 985 A1 | 11/2006 |

OTHER PUBLICATIONS

German Search Report with English language translation dated Oct. 13, 2010 (nine (9) pages).
European Search Report with English language translation dated Jun. 30, 2011 (six (6) pages).

* cited by examiner

*Primary Examiner* — Paul West
(74) *Attorney, Agent, or Firm* — Crowell & Moring LLP

(57) ABSTRACT

A device for sampling cultures such as microorganisms or cells via a connection (10) from autoclavable culture vessels, including a sterile syringe for receiving the sample and having a so-called Luer Lock taper and an automatic valve (8) that automatically opens when the syringe is attached and automatically closes when the syringe is detached, and further including a first check valve (41) closing towards the automatic valve (8) and provided between the automatic valve (8) and the connection (10).

4 Claims, 1 Drawing Sheet

SAMPLING DEVICE

CROSS REFERENCE TO RELATED APPLICATIONS

This application claims priority from Federal Republic of Germany patent application no. DE 10 2009 043 699.5, filed Oct. 1, 2009, the entire disclosure of which is incorporated herein by reference.

BACKGROUND OF THE INVENTION

The present invention relates to a generic device for taking a sample, that is, a device for sampling culture solutions such as microorganisms (e. g. bacteria, yeasts, fungi) or cells (e. g. mammal and insect cells) via a connecting tube from preferably autoclavable culture vessels such as bioreactors or disposable cultivation systems such as plastic bags or pouches for cultivating microorganisms or cells using a sterile syringe receiving the sample and having a so-called Luer Lock taper and an automatic valve that automatically opens when the syringe is attached and automatically closes when the syringe is detached, also referred to as an injection site.

Cultivations of bacteria, yeasts, fungi and animal cells as well as mammal cells are performed on a small scale, i. a. in autoclavable bioreactors and disposable plastic bags (DE 10 2004 045 916 A1). During the cultivation, it is necessary to sample the culture, e. g. in order to be able to determine growth parameters. When samples are taken, it must be ensured that a contamination of the culture vessel by external germs is avoided.

Such generic device is known. This sterile technical solution known to date makes use of an automatic valve that automatically opens when the sterile syringe comprising the Luer taper is attached and automatically closes when the syringe is detached. Such automatic valves ("injection site") are common and established in medical technology for adding or withdrawing fluids, for example, for the use on infusion sets, blood bags etc., and are available from various manufacturers on the market.

However, the generic device is disadvantageous regarding several aspects. Namely, it enables the addition as well as the withdrawal of fluids, for example, which is not desired in the use for the sample collection because the unwanted addition of fluids might contaminate the culture vessel. Thus, there is the risk of a faulty operation during the use for sampling. After the sample collection, the automatic valve and the connecting tube connected thereto and to the culture vessel remain filled with a culture solution forming the sample which results in the fact that the system has to be "rinsed" before the next sample collection. During this process, a particular amount of fluid must first be withdrawn and rejected before the actual sample can be taken. This may give rise to a problem in culture vessels of small volumes because too much volume is lost to rinsing. All in all, the known device presents itself as useful only to a limited degree.

SUMMARY OF THE INVENTION

It is therefore the object of the invention to provide an improved sampling device which is less problematic regarding function and effectiveness.

Thus, in a generic device of the type described above, this object is achieved by the invention as described and claimed hereinafter in that between the automatic valve and the connection a first check valve closing towards the latter is provided.

According to the teaching of the invention, due to the first check valve it is possible to collect a sample via the connection by using the sterile syringe, but it is not possible, however, to introduce fluids in the reverse flow direction. Thus, sterile sampling without contaminating the culture is made possible for the first time vis-à-vis the prior art.

In one advantageous further embodiment of the invention, a T piece connecting the connection via a through conduit and having a stub is disposed between the automatic valve and the connection; the first check valve closing towards the T piece is provided in the through conduit, and a second check valve opening towards the T piece is disposed in the stub. In this arrangement the second check valve not only automatically closes to prevent the introduction of culture solution into the stub; furthermore, after the sample collection the device can practically be emptied completely with sterile air so that it is thus all but dead volume-free. Finally, the inventive device merely allows the introduction of air via a preferably provided sterile filter, but does not allow the withdrawal of the culture solution, which would damage the sterile filter. Therefore, according to the teaching of the invention, sampling by using the sterile syringe is possible via the through conduit, however, the supply of fluids in the reverse flow direction is not possible due to the two check valves.

To this end the sampling is performed such that the sterile syringe is attached to the automatic valve, and the plunger thereof is pulled out to take the sample. After that, the sterile syringe is detached from the automatic valve. Due to the second check valve opening towards the T piece in the stub, the sample cannot get into the stub. Next, the plunger of a second syringe—which may be unsterile—provided at the end of the stub is pulled out to fill the syringe with air, and after connection to the stub having an air filter, it is squeezed out so often until the culture solution still present between the T piece and the connection to the culture vessel is forced back into the latter.

Thus, in a surprisingly simple manner, the new sampling device according to the invention enables aseptic sample collection in a very simple fashion. It offers the possibility to replace the culture solution in the device by sterile air after the sampling, whereby it is no longer necessary to subsequently rinse the sampling device and reject or discharge the culture solution as has been necessary in the past. This is of great importance, particularly for small culture vessels in which the culture volume remaining in the culture vessel could be reduced below a critical value due to the sampling.

Operating errors are also constructively excluded because the flow directions are clearly defined by the check valves. Thus, an accidental contamination of the culture vessel via the sampling is not possible either. It is even possible to carry out a sterile further processing of the samples. The dead volume may be reduced to less than 0.1 ml, which represents a negligibly small value. It also is a great advantage that the system can be autoclaved several times.

Finally, the undesired introduction of culture solution into the air filter by the invention is not possible according to the construction. In addition, the manual blockage of the sample collection is no longer necessary since this will be taken over by the automatic valve. However, according to the teaching of the invention, it is also possible to manage the measurement without the two check valves, in that case with less comfort, if the automatically operating check valves are replaced by manual cut-off valves or at least the stub is manually cut off during sampling, for example by a cut-off valve or a hose clamp.

It is a particular advantage that in the inventive device the sterile syringe comprising the Luer Lock taper, the second syringe, the automatic valve, the T piece, the stub, the first check valve, the second check valve, the piece of tube, the air filter and/or the connecting tube as a system may consist of known, commercially available components that can be combined with one another and are delivered as a set, optionally assembled in part, so that they can be assembled to form the device in a very unproblematic, inexpensive and easy manner.

Further suitable designs and refinements of the invention are described hereinafter.

BRIEF DESCRIPTION OF THE DRAWINGS

The invention will be described in further detail hereinafter with reference to the accompanying drawings, in which.

DETAILED DESCRIPTION OF PREFERRED EMBODIMENTS

Figure 2:
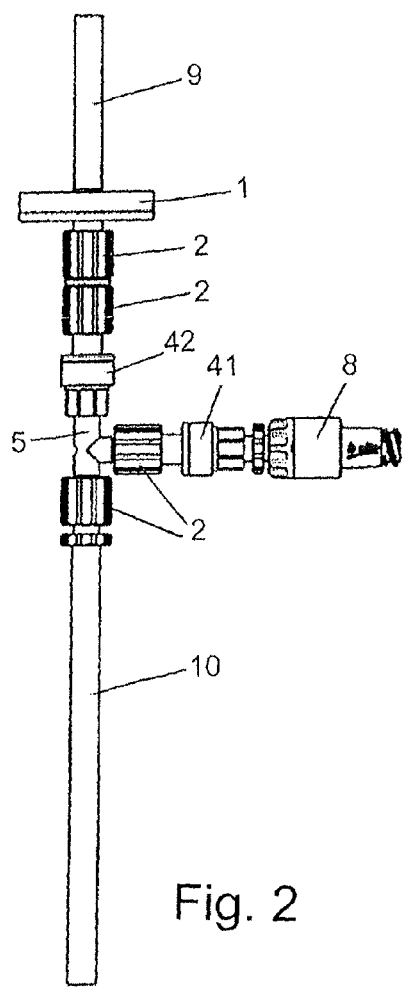
FIG. 2 shows the sampling device of the invention in an assembled condition.
Figure 1:
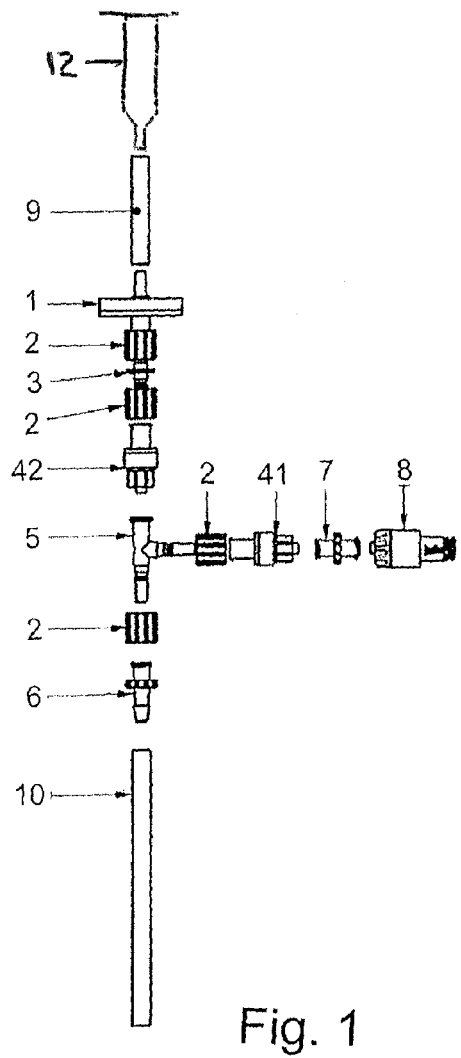
FIG. 1 shows the sampling device of the invention in an exploded view.

The device shown in FIG. 1 serves to sample cultures such as microorganisms or cells via a connection 10 formed as a connecting tube leading from one or more autoclavable culture vessels (not shown) by using a sterile syringe for receiving the actual sample and having a so-called Lock Luer taper via an automatic valve 8 that automatically opens when the syringe is attached and automatically closes when the syringe is detached.

Between the automatic valve 8 and the connection 10, a T piece 5 is disposed that connects the latter via a through conduit and comprises a stub having an air filter 1. At the end of the stub a second syringe 12 (schematically illustrated) can be connected via a piece of tube 9. A first check valve 41 closing towards the T piece 5 is provided in the through conduit, and a second check valve 42 opening towards the T piece is disposed in the stub.

In the device according to the invention, preferably the sterile syringe comprising the Luer Lock taper, the second syringe, the automatic valve 8, the T piece 5, the stub, the first check valve 41, the second check valve 42, the piece of tube 9, the air filter 1 and/or the connecting tube 10 are formed as commercially available components known per se that can be combined with one another and are delivered as a set, so that they can be assembled into the device in a simple manner.

In this course, the air filter 1 is locked onto a finger ring 2 with a Luer Lock locking, which finger ring 2 is connected to a male/male Luer connector 3 that in turn is connected to a finger ring 2 for connection to the second check valve 42. The reference numeral 7 denotes a female/female Luer connector, and reference numeral 6 denotes a female Luer connector/hose nipple structure.

In such a sample collection device, the sample collection is performed such that the sterile syringe is attached to the automatic valve 8, and the plunger thereof is pulled out to take the sample. After that, the sterile syringe is detached from the automatic valve 8. Due to the second check valve 42 opening towards the T piece 5 in the stub, the sample cannot get into the stub. Next, the plunger of the second syringe—which also may be unsterile—provided at the end of the stub is pulled out to fill the syringe with air, and after connection to the stub having the air filter 1, it is squeezed out so often until the culture solution still present between the T piece 5 and the connection 10 to the culture vessel has been forced back into the latter.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A device for sampling cultures via a connection from an autoclavable culture vessel, said device comprising
   a sterile syringe for receiving a sample, said syringe having a Luer Lock taper, and
   an automatic valve that automatically opens when the syringe is attached and automatically closes when the syringe is detached,
   wherein
   a first check valve is provided between the automatic valve and the connection,
   said first check valve closes away from the automatic valve,
   a T piece connecting the connection via a through conduit and comprising a stub disposed between the automatic valve and the connection,
   the first check valve closing towards the T piece is provided in the through conduit,
   a second syringe is provided at the end of the stub, the second syringe having a plunger arranged to be pulled out to fill the second syringe with air prior to connection of the second syringe to the stub and to be pushed in after connection of the second syringe to the stub such that the air in the second syringe forces culture solution still present between the T piece and the connection to the culture vessel back into the culture vessel, and
   a second check valve opening towards the T piece is provided in the stub;
   further comprising an air filter disposed in the stub, the air filter being locked onto a finger ring with a Luer Lock locking, said finger ring being connected to a Luer connector that in turn is connected to a finger ring for connection to the second check valve.

2. A device according to claim 1, wherein the second syringe at the end of the stub is connectable via a piece of tube.

3. A device according to claim 1, wherein the connection is formed as a connecting tube.

4. A device according to claim 1, wherein said culture is a microorganism culture or a cell culture.

* * * * *